United States Patent [19]

Kurtz et al.

[11] 4,449,395

[45] May 22, 1984

[54] PHEOLOGICAL MEASUREMENT METHOD AND APPARATUS

[75] Inventors: Stuart J. Kurtz, Martinsville, N.J.; Terry A. De Rossett, Hastings-on-Hudson, N.Y.; Montgomery T. Shaw, Mansfield Center, Conn.

[73] Assignee: Union Carbide Corporation, Danbury, Conn.

[21] Appl. No.: 366,723

[22] Filed: Apr. 8, 1982

[51] Int. Cl.³ .................................... G01N 11/04
[52] U.S. Cl. .................................................. 73/56
[58] Field of Search .............................. 73/56, 54

[56] References Cited

U.S. PATENT DOCUMENTS

| | | | |
|---|---|---|---|
| 2,780,096 | 2/1957 | Noble et al. | 73/56 X |
| 3,252,320 | 5/1966 | Welty | 73/56 |
| 3,526,126 | 9/1970 | Wilchinsky et al. | 73/56 |
| 3,595,305 | 7/1971 | Welty et al. | |
| 3,832,886 | 9/1974 | Ptiskin | 73/56 |
| 3,841,147 | 10/1974 | Coil et al. | 73/56 |
| 4,229,970 | 10/1980 | Barker et al. | 73/56 |
| 4,241,602 | 12/1980 | Han et al. | 73/56 |

FOREIGN PATENT DOCUMENTS

| | | | |
|---|---|---|---|
| 2715643 | 10/1978 | Fed. Rep. of Germany | 73/56 |
| 255640 | 3/1970 | U.S.S.R. | 73/56 |

Primary Examiner—Gerald Goldberg
Assistant Examiner—Joseph W. Roskos
Attorney, Agent, or Firm—Gerald R. O'Brien, Jr.

[57] ABSTRACT

Method and apparatus for testing thermoplastic material comprising: passing as a stream a fractional, continuous, molten and flowable sample of the material to and successively through each of either a controllable pumping zone maintained at constant temperature and pressure or controllable pressure zone maintained at constant flow rate and temperature, and a die zone to form a continuous strand of the material; measuring the viscosity of the material in the pumping and die zones; providing a measurement of elasticity by obtaining a measurement of percentage of cross-section area swell in the strand in passage from the die zone over a constant length distance downstream of a point of strand marking to a point of strand marking to a point of mark sensing; and combining the viscosity measurement with the elasticity measurement to provide fuller rheological characterization data for the material.

4 Claims, 1 Drawing Figure

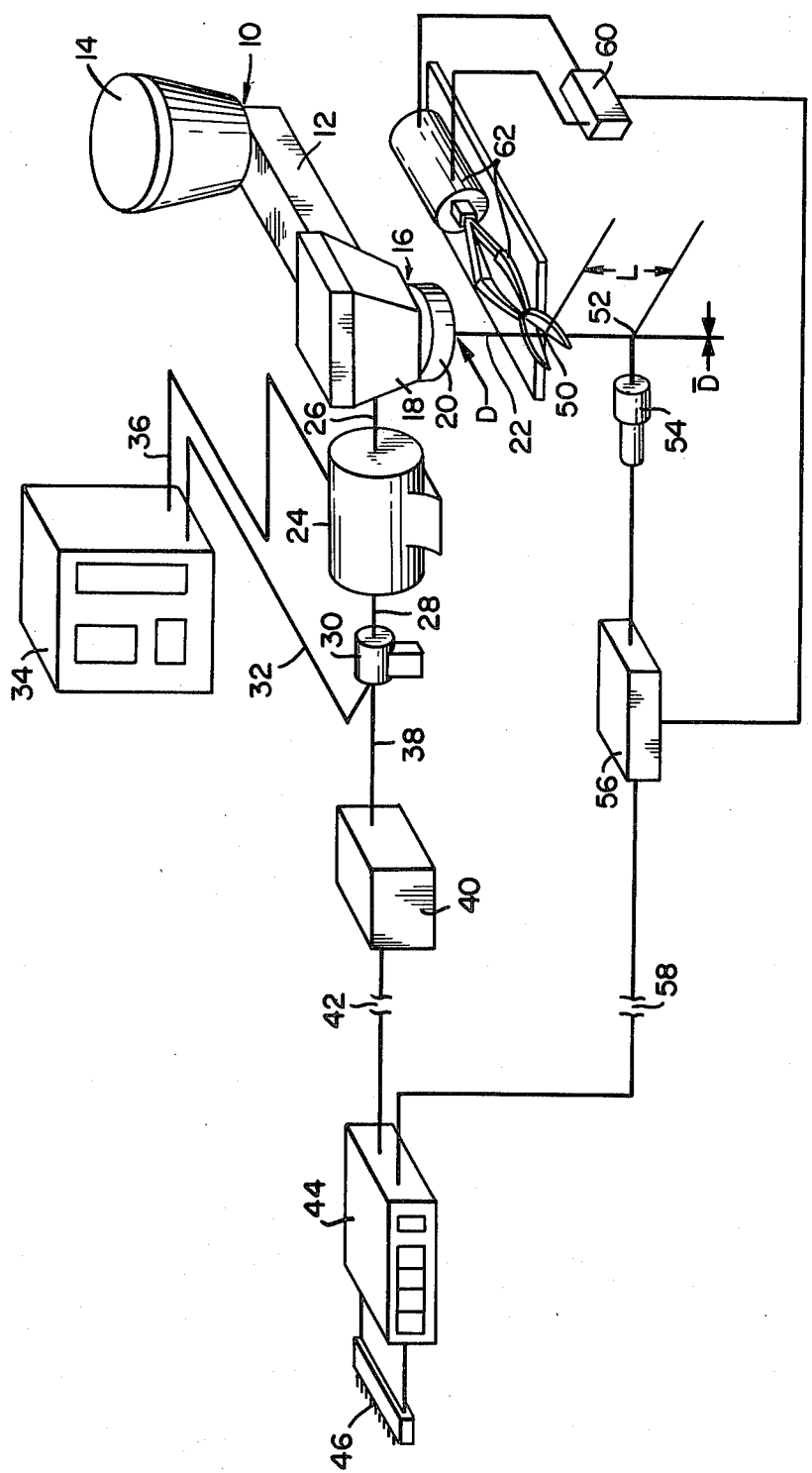

RHEOLOGICAL MEASUREMENT METHOD AND APPARATUS

The present invention relates to a rheological measurement method and apparatus and, more particularly, to such method and apparatus for testing a product stream of molten thermoplastic material to obtain a viscosity measurement and an elasticity measurement for said material.

The problem to be resolved was how to measure rheological parameters needed for characterizing and predicting polymer properties and also using that data for reactor control and compounding line control by a feedback system. Elasticity was selected as the property which used with viscosity could be employed for those purposes. Viscosity has been measured but that polymer property would not be completely sufficient for reactor and compounding line control. The addition of the measurement of elasticity offers the greatest potential to achieve these aims.

There are various measurements of elasticity and among these considered included entrance pressure loss, normal stress and die swell; the latter in conjunction with such instruments as the Seiscor continuous melt (SCM) indexer described hereinbelow. Others have measured die swell but not in the manner of this invention.

Die swell of polymeric materials can be measured by use of a capillary rheometer in which the sample material is extruded, presumably at a predetermined constant rate and temperature, through a die. Die swell can be measured isothermally or after the material has cooled.

One particular method of measuring die swell, in the past, was to place the material into an extrusion chamber, heat to an equilibrium temperature and to extrude it at a predetermined constant rate through a die. After cooling, the extrudate is cut into a fixed length, accurately weighed and its density measured. Die swell is then calculated as the ratio of the cross-sectional area of the extrudate to the cross-sectional area of the die. The cross-sectional area of the extrudate is calculated as:

$$A = \frac{\text{extrudate weight/density of extrudate}}{\text{extrudate length}}$$

This method is accurate but time consuming, prone to calculation errors and not suitable for control purposes.

Another approach is discussed in U.S. Pat. No. 3,832,886 which is based on the equation of continuity for incompressible fluids. That patent states that material is extruded at constant velocity through a circular die. The compound swells as it leaves the die and results in an increased area and an associated velocity decrease. When the volumetric flow rate is constant, die swell is the ratio of diameters or the square root of areas or the inverse of the square root of velocities. The teaching of U.S. Pat. No. 3,832,886 is that, because the velocity is a function of the elasticity (or die swell) of the material, the die swell can be measured by determining the time it takes for the extrudate to move a fixed distance. The definition of die swell is:

$$S = \frac{\text{cross-section area of extrudate}}{\text{cross-sectional area of die}}$$

The patent states that by selecting the distance to have the same numerical value as the velocity the constant in the equation becomes unity. That is:

$$S=(u/d)t,$$

where
  u is the velocity of material,
  d is the fixed distance
  t is the time the material takes to move distance d;
or
  S=(constant) t, with the constant equal to one.

Therefore, it is concluded that die swell can be measured directly. The length of the extrudate was measured by a timer which was activated when light beams, aimed at photocells at a fixed distance apart, are blocked by the moving extrudate.

It is believed that it would be advantageous to meet the following four conditions in achieving the measurement of die swell:
1. The measurement of die swell should not interfere with the determination of viscosity, eg. melt index;
2. It should be automatic and done frequently.
3. It should be accurate and independent of the resulting sample cross-sectional shape or uniformity.
4. The equipment needed for this purpose is commercially available.

It has been found that all four criteria were not met by prior systems. However, since the SCM is commercially available, which continuously measures melt index and flow index directly on production or pilot equipment, such equipment can be employed for use as a component of apparatus for measuring fuller rheological characteristics.

Melt flow ratio is related to molecular weight distribution and elasiticity; however, it has proven to be an extremely poor measure of elasticity.

$$\text{Melt flow ratio} = \frac{\text{flow index}}{\text{melt index}}.$$

Die swell is a far better measure of elasticity. The SCM equipment is suited for the task but extensive attachments ae required for incorporation into the apparatus of the present invention.

The Seiscor Rheometer Model AK-400 continuous melt rheometer (SCM) is manufactured by the Seiscor Division of Seismograph Services Corporation, Tulsa, OK under liscense of U.S. Pat. Nos. 3,252,320 and 3,595,305 of Philips Petroleum Company.

For informational and background purposes, a brief description of the SCM operating concepts follow.

As stated in the Seiscor operating manual, which is incorporated herein as a reference, " . . . a closed loop control system maintains a constant pressure drop (constant shear stress) across measurement capillary by varying the polymer flow rate through it. Polymer flow rate is then a function of the shear rate through the capillary and polymer viscosity. Polymer flow is measured by a tachometer directly coupled to the metering pump drive motor. Pump speed can therefore be calibrated in such terms as shear rate, melt flow, melt index, high melt index, CIL units, or correlated to other types of viscosity or flow data (depending on polymer type, and test parameters such as control pressure, flow density, pump size, temperature, capillary geometry, etc.)."

In the SCM, "polymer melt from the process enters the die unit metering pump which is driven by a variable speed DC motor. The polymer flows through the flow passage barrel (with sufficient residence time for the polymer to be brought to the required test temperature) into the test cavity containing the pressure transducer, and finally through the capillary orifice. The transducer measures the pressure drop across the capillary; this signal is compared to the set point pressure (control pressure), and the resulting error is amplified by the motor speed controller to regulate the speed of the DC motor that drives the metering pump. Both pressure and speed signal-pressure pen, speed signal-speed pen)."

"The Dual Cavity Die Unit has two test cavities. Each cavity can have a different transducer/capillary arrangement and thus provides two independent shear tests on the polymer. Flow can be diverted into either of the cavities by manual selection or by program control based on a 20 minute time cycle where the polymer flows through cavity "A" for a part of the cycle then through cavity "B"."

In accordance with the present invention, a method is provided for testing a product stream of molten thermoplastic material to obtain a viscosity measurement and an elasticity measurement for said material comprising: passing a fractional, continuous, molten and flowable sample of such stream of said material to and successively through each of either a controllable pumping zone maintained at constant temperature and pressure or controllable pressure zone maintained at constant flow rate and temperature, and a die zone to form a continuous strand of such material; measuring the viscosity of said material in said pumping and die zones; providing a measurement of elasticity by obtaining a measurement of percentage of cross-section area swell in said strand in passage from said die zone over a constant length distance downstream of a point of strand marking to a point of mark sensing; and combining said viscosity measurement with said elasticity measurement to provide fuller rheological characterization data for said material.

To measure the desired polymer properties an extrudate must be provided. This has been accomplished by use of a continuous melt rheometer. Other means may be used to do the same operation. The SCM apparatus is not unique by today's standards but does constitute the best apparatus made for accomplishing the melt index measurement task.

Polymer must be fed to the SCM unit which consists of two basic sections, a control unit and a die unit. If the polymer is molten, it can be fed directly to the die unit. If the polymer is solid, it must be processed by a plasticating extruder.

The die unit yields two streams of polymer that may be tested. This invention defines additions to the SCM apparatus required to provide the means of obtaining rheological data that supplements its basic capability of measuring melt index and flow index.

The devices which are the subject of this invention operate on the extrudates from the SCM die unit. Further, it is necessary to provide a means for cutting or merely identifying the time interval for the polymer strand to travel a specific length from which its average diameter is calculated. Die swell is then determined by comparing the rheometer die diameter with the average strand diameter after leaving the die in its enlarged form.

When a strand cutter is used, a predetermined length of extrudate is cut. By measuring gear pump rotation (in the SCM) and time between cuts, or the marked lengths, the extrudate volume and/or volume flow rate may be determined. The average strand diameter, $\overline{D}$, may be calculated by the formula:

$$\overline{D} = 2\sqrt{\frac{TQ}{L}} = 2\sqrt{\frac{V}{IIL}},$$

where:
T = time between cuts
Q = volume flow rate of extrudate
L = length of strand (distance between cuts)
V = volume pumped between cuts (= TQ)

Unlike other measurements, such as direct diameter measurement by scanning lasers, the present invention does not require for accuracy a strand of circular cross-section. In fact, under normal circumstances the extrudate from the cylindrical capillary of the SCM may actually be elliptical in cross section. When a laser, such as disclosed in U.S. Pat. No. 4,229,970, is used, it may measure directly extrudate thickness. However, this technique requires a "take-off" device to prevent gravity stretching of long extrudates thus changing strand thickness; (e.g. slowly rotating platform or a conveyor below the die to prevent stretching or extrudate buildup). This technique is further complicated by the shape of the strand which may not be circular in cross-section.

For either of the methods listed above, cutting the strand of a specified length, or laser measurement (only for circular cross-section strands), percent die swell may be calculated as:

$$S = \left(\frac{\overline{D} - D_o}{\overline{D}}\right) \times 100$$

where:
$D_o$ = rheometer die diameter
$\overline{D}$ = strand diameter
S = percent die swell As stated previously, the U.S. Pat. No. 3,832,886 system teaches that the material is initially housed in a cylinder. A piston moving at constant velocity forces the material through a die. When the material exits from the die, the time (t) it takes the material to move a distance (d) is measured by an electronic timer. The timer is activated when light beams, aimed at photocells a distance (d) apart, are blocked by the moving extrudate. By selecting the distance, d, to have the same numerical value as the velocity, V, the constant in the equation:

$$S = (V/d)t = (\text{constant})t,$$

becomes unity and the die swell becomes numerically equal to the time measurement. To distinguish this patent from the present invention it is to be noted that:

A. The prior patented system must be adjusted to operate at a constant velocity and we operate a constant pressure source. In the instant invention, the control loop provides feedback to adjust the volumetric flow rate to maintain constant pressure. Also the die swell is measured automatically and frequently at constant pressure, as compared with the patent system measurement at a presumed constant velocity and as an intermittent determination. Die swell measurement by the two systems will differ in general but there are instances when they will agree.

B. In the instant invention, the measurement of die swell is based on a continuous stream of extrudate at constant pressure so the consistency of the material is of little concern. In the preferred configuration of the prior patent the process is not at steady state in that the die pressure will change with time. Two factors will cause this to be non-steady state, material residence time or consistency and the process itself.

C. The instant invention, no assumption of constant volumetric flow rate over time is made, we integrate the instantaneous flow rate to overcome problems associated with the assumption of constant volumetric flow rate. The process of the invention gives the most accurate measure of the average die swell.

D. Cutting the strand or extrudate also provides a means of disposing of the polymer build-up at the testing apparatus when actually utilized in production units.

Apparatus suitable for practicing the process aspect of the invention is set forth in the single FIGURE of the drawing which is a schematic representation of an electro-mechanical diagram thereof.

As shown, apparatus 10 is provided for supplying thermoplastic polymer as a melt at a temperature above its melting point and glass transition temperature. This may be a plasticating extruder 12 if resin is supplied to feed hopper 14 at a temperature below its melting point or glass transition temperature. A constant displacement pump unit 16, preferably having a metering pump 18 of the gear pump type, is provided which accurately meters polymer melt to die 20 to form a strand of any cross-sectional shape 22 for subsequent analysis. A motor 24 is directly shafted 26 to drive the metering pump 1. The motor speed can be controlled by a feedback loop through 32, 34, 36 to provide constant pressure in the die 20 or can provide constant speed by fixing the rotation speed of the motor 24.

A tachometer generator 30 produces a voltage signal proportional to RPM which is employed to accurately measure the speed of the motor 24 (revolutions per minute). This signal can be used both to measure speed and for feedback control of motor 24. An electrical unit is provided to convert the analogue electrical signal to a form useful for integration. This can be to a digital signal or, most preferably, as a frequency proportional to the voltage known as a V/F converter 40. This signal is then fed into a line driver (not shown) for transmission through remote line 42 to a digital integrator 44. The integration can be handled in this latter case by counting the cycles (known as frequency counter operation mode). Thus, an integrated signal is obtained in itegrator unit 44.

Integrator unit 44 will present a digital integrated signal which is proportional to the flow volume (of polymer) of the melt pump 18. To integrate properly, a lower and upper limit must be specified. This is done by signaling when the sample is to be measured at a mark point 50. The mark can be produced by cutting the extrudate strand at the starting time. (This is the lower limit). Integration proceeds until the strand reaches position 52 at which point a sensor, preferably a fiber optic device 54, sends a signal via 56 through remote line 58 to the integrator 44 to arrest the integration operation. Simultaneously, a signal is given from the relay 56 to the solenoid 60 which produces the next mark on the strand, preferably to cut the strand via a shear cutting device (scissors) or the like 62, thus beginning another cycle. The previous integration is "latched" and available at integrator 44 while the integration of the next cycle proceeds.

The computed signal from 44, which is proportional to the volume extruded in that time period, can be sent by digital or other signal to a display and/or recording device through output connectors 46. This information can be used in calculations to give a measured die swell along with the melt index, simultaneously. Thus, both an elasticity and viscosity measurement can be obtained.

If it is to be understood that the apparatus described hereinabove and shown schematically in the embodiment of the drawing comprises a number of component elements or units which are available commericially and are well known to those skilled in the instrumentation arts. Accordingly, no ultimate descriptions will be set forth for the internal construction or circuitry of these component units themselves.

What is claimed is:

1. The method for testing a product stream of molten thermoplastic material to obtain a viscosity measurement and an elasticity measurement for said material comprising: passing a fractional, continuous, molten and flowable sample of such stream of said material to and successively through each of either a controllable pumping zone maintained at constant temperature and pressure or controllable pressure zone maintained at constant flow rate and temperature, and a die zone to form a continuous strand of such material of any resultant shape; measuring the viscosity of said material in said pumping and die zones; providing a measurement of elasticity by obtaining a measurement or percentage of cross-section area swell in said strand in passage from said die zone over a constant length distance downstream of a point of strand marking to a point of mark sensing; and combining said viscosity measurement with said elasticity measurement to provide fuller rheological characterization data for said material.

2. The method for testing a product stream of molten thermoplastic material to obtain a melt or flow index viscosity meaasurement and an elasticity measurement for said thermoplastic material comprising: passing a fractional, continuous molten and flowable sample of such stream of said thermoplastic material to and successively through each of either a controllable rheological indexer pumping zone at a constant temperature and pressure or controllable pressure zone maintained at constant flow rate and temperature, and die zone to form a continuous strand of such material of any resultant cross-sectional shape; measuring the melt or flow index of said thermoplastic material in said rheological indexer pumping and die zones; cutting said strand of such thermoplastic material downstream of said die zone to form cutting of substantially constant length equal to the distance between the point of cutting and a point of sensing; providing a measurement of elasticity by obtaining a measurement of percentage of cross-sectional area swell in said cutting in passage from said die zone over said constant length distance downstream of the point of strand cutting; and combining said viscosity measurement with said elasticity measurement to provide fuller rheological characterization data for said thermoplastic material.

3. The method for testing a product stream of molten thermoplastic material to obtain a viscosity measurement and an elasticity measurement for said thermoplastic material comprising: passing a fractional, continuous, molten and flowable sample of such stream of said material to and successively through each of either a controllable pumping zone maintained at constant temperature and pressure or controllable pressure zone maintained at constant flow rate and temperature, and a die zone and forming a continuous strand of such thermoplastic material of any resulting cross-sectional shape; measuring the viscosity for said thermoplastic material in said pumping and die zones; cutting said strand of such thermoplastic material downstream of said die zone to form cuttings of substantially constant length equal to the distance between the point of cutting and a point of sensing; providing a measurement of elasticity by obtaining a measurement of percentage of cross-sectional area swell in said cuttings in passage from said die zone over said constant length distance downstream of the point of strand cutting; measuring the volume of thermoplastic material of said strand cuttings by integration of electrical signals proportional to the volumetric flow rate thereof and employing said measurement to electrically coordinate said elasticity measurement to provide fuller and more accurate rheological characterization data for said thermoplastic material.

4. Apparatus for testing a product stream of molten thermoplastic material to obtain a viscosity measurement and an elasticity measurement for said thermoplastic material comprising: means for passing a fractional, continuous molten and flowable sample of such stream of said thermoplastic material to and successively through each of either a controllable pumping zone maintained at constant temperature and pressure or controllable pressure zone maintained at constant flow rate and temperature; a die zone to form a continuous strand of such thermoplastic material of any resulting shape; means for measuring the viscosity of said thermoplastic material in said pumping and die zones; means for providing a measurement of elasticity by obtaining a measurement of percentage of cross-section area swell in said strand in passage from said die zone over a constant length distance downstream of a point of strand marking to a point of mark sensing; and means for combining said viscosity measurement with said elasticity measurement to provide full or rheological characterization data for said thermoplastic material.

* * * * *

UNITED STATES PATENT AND TRADEMARK OFFICE
CERTIFICATE OF CORRECTION

PATENT NO. : 4,449,395
DATED      : May 22, 1984
INVENTOR(S): S.J. Kurtz et al

It is certified that error appears in the above-identified patent and that said Letters Patent is hereby corrected as shown below:

Title, Title page and Column 1:
    "PHEOLOGICAL" should be --RHEOLOGICAL--.

Column 2, line 36:
    "elasiticity" should be --elasticity--.

Column 2, line 44:
    "ae" should be --are--.

Column 5, line 36:
    "1" should be --18--.

Column 6, line 33:
    "or" should be --of--.

Column 8, line 22:
    "full" should be --fuller--.

Signed and Sealed this

Eighteenth Day of September 1984

[SEAL]

Attest:

GERALD J. MOSSINGHOFF

Attesting Officer

Commissioner of Patents and Trademarks